United States Patent [19]

Moses

[11] 4,114,609
[45] Sep. 19, 1977

[54] LARYNGOSCOPE

[76] Inventor: John A. Moses, 30 Kalan Cir., Fairfield, Conn. 06430

[21] Appl. No.: 778,427

[22] Filed: Mar. 17, 1977

Related U.S. Application Data

[63] Continuation-in-part of Ser. No. 596,356, Jul. 16, 1975, abandoned.

[51] Int. Cl.² .............................................. A61B 1/06
[52] U.S. Cl. ....................................................... 128/11
[58] Field of Search ..................................... 128/10–18

[56] References Cited

U.S. PATENT DOCUMENTS

| 2,354,471 | 7/1944 | MacIntosh | 128/10 |
| 3,426,749 | 2/1969 | Jephcott | 128/11 |
| 3,856,001 | 12/1974 | Phillips | 128/11 |
| 3,943,920 | 3/1976 | Kandel | 128/11 |
| 3,986,854 | 10/1976 | Scrivo et al. | 128/11 |

Primary Examiner—Robert W. Michell
Assistant Examiner—Henry S. Layton
Attorney, Agent, or Firm—Arthur T. Fattibene

[57] ABSTRACT

A laryngoscope blade comprising an essentially straight blade portion have the inner end portion which is curved out of the plane of the straight blade portion, and which curved portion is adapted to be received in the groove defined between the base of the tongue and the epiglottis of a patient whereby the tip end causes the tongue to be moved anteriorly to expose the inlet of the larynx and the straight portion of the blade defines a line of sight directly into the larynx.

3 Claims, 7 Drawing Figures

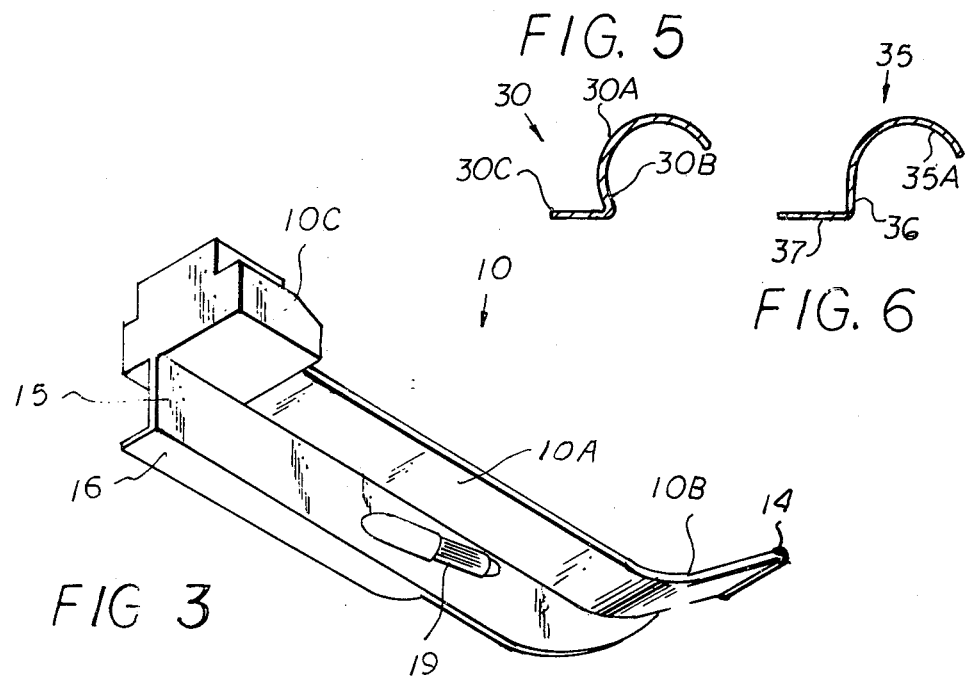
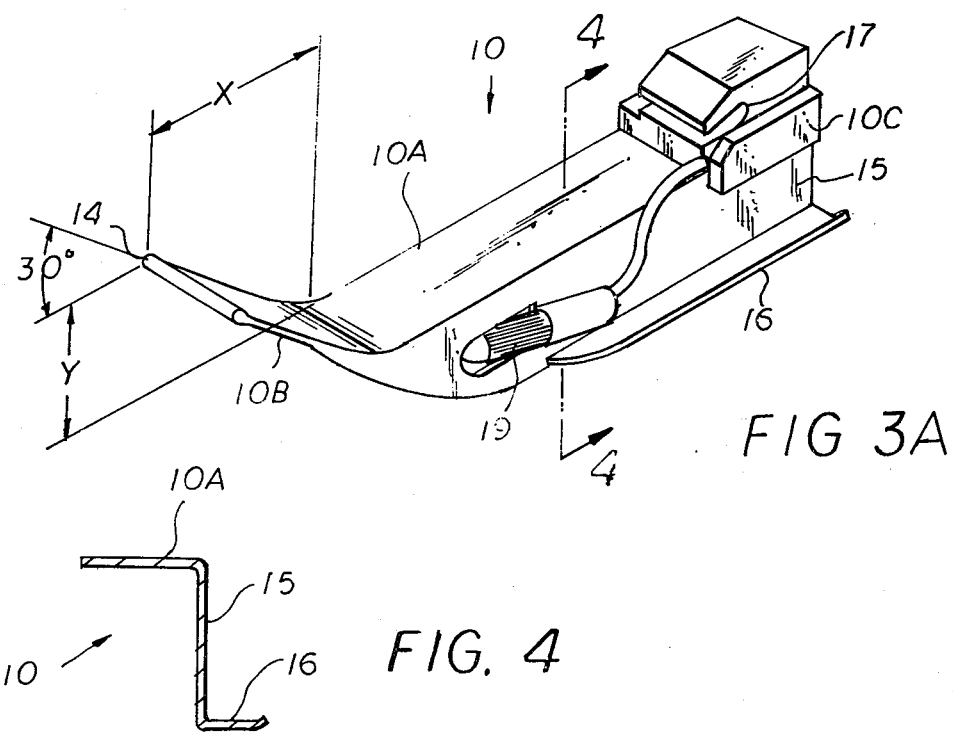

LARYNGOSCOPE

RELATED APPLICATION:

This application is a continuation in-part application of my application Ser. No. 596,356 filed July 16, 1975 for Laryngoscope, now abandoned.

BACKGROUND OF THE INVENTION

Laryngoscopes are used by doctors for visualization of the larynx and for endrotracheal intubation, the latter being frequently employed in the practice of anesthesiology. The tube which is inserted during an endrotracheal intubation keeps a patient's airway patent or open without obstruction. The procedure also enables an anesthesiologist to ventilate the lungs of a patient. The endotracheal tube is also employed in the practice of resuscitation of the critically ill and unconscious patients. The endotracheal procedure is also used to protect a patient from aspirating gastric contents into his lungs. Thus, the exposure and visualization of the larynx with the aid of a laryngoscope is essential for the procedure of endotracheal intubation in most instances. The rare exceptions are those instances where blind intubation, i.e., intubation without a laryngoscope, is indicated.

PROBLEM AND PRIOR ART

A laryngoscope as used in anesthesiology usually consists of a handle portion in which the batteries for the illumination of the laryngoscope are housed and a laryngoscope blade connected at right angles to the handle about a detachable hinge joint. Heretofore, the known laryngoscope blades are the so called straight blades of the type disclosed in U.S. Pat. Nos. 3,856,001; 2,433,705; and 2,289,226, and the curved blade of the Macintosh type disclosed by U.S. Pat. No. 2,354,471. Other blades such as the Wisconsin blade, Robertshaw blade, and Miller blade, are also known. However, these latter blades are similar to the so called straight blades.

The straight blades which preceeded the Macintosh blade, had an inner end which was designed to pass underneath the epiglottis and which the epiglottis was then lifted to expose the larynx. This technique frequently resulted in the blade touching the lower surface of the epiglottis which is innervated by the vagus nerve. When this occurred, harmful reflexes could be initiated through the excitment of the vagus nerve during laryngoscopy, unless the anesthesia is deep. As deep anesthesia can be harmful to a patient; deep anesthesia during most laryngoscopy is not desirable.

Another difficulty encountered with the use of the so called straight laryngoscope blade is that the epiglottis frequently sliped off the inner end of the blade when the procedure was attempted. As a result, repeated attempts had to be made to lift up the epiglottis correctly. The use of the straight blades thus presented some difficulties.

To obviate the difficulties noted with the straight laryngoscope blades, a curved blade of the Macintosh type was developed. The curved blade is curved throughout the length thereof, with its inner end shaped to be inserted into the groove between the base of the tongue and the epiglottis. While the curved blade thus functional to move the tongue anteriorly to expose the larynx, the exposure or visibility of the larynx was still obscured due to the curvature of the main portion of the curved blade. The central curvature of the curved blade obstructed the vision by protruding into the line of sight to the larynx.

OBJECTS

An object of this invention is to provide an improved laryngoscope blade which is capable of moving the tongue anteriorly to expose the larynx, and which will not interfere with the line of sight into the larynx.

Another object is to provide an improved laryngoscope blade to facilitate endotracheal intubation and which will provide for maximum exposure of the larynx.

BRIEF SUMMARY OF THE INVENTION

This invention is directed to a laryngoscope blade which comprises an essentially straight blade portion having the inner end portion curved so as to be received in the groove defined between the base of the tongue and the epiglottis so that the base of the tongue can be moved anteriorly to expose the inlet of the larynx. The arrangement is such that the essentially straight portion of the blade provides an unobstructional line of sight directly into the larynx. The laryngoscope blade is also provided with a bulb for illumination and which bulb is connected in circuit to batteries carried in the handle portion of the laryngoscope.

In the drawings:

FIG. 3 is a perspective view of the laryngoscope blade of this invention.

FIG. 3A is another perspective view of the blade of this invention.

FIG. 4 is a detailed sectional view taken along line 4—4 in FIG. 3.

FIG. 5 is a detailed sectional view of a modified construction.

FIG. 6 is a detailed sectional view of another modified construction.

DETAILED DESCRIPTION

Figure 2:
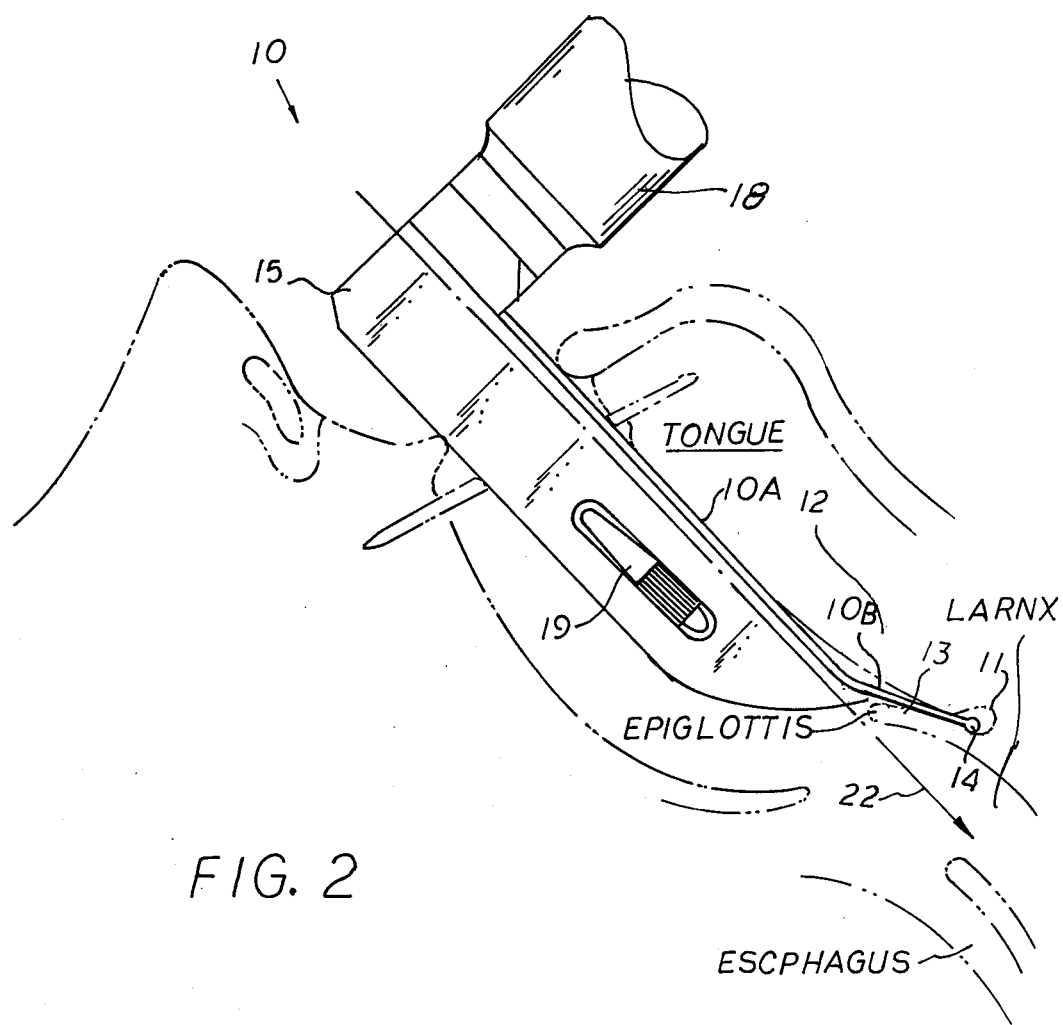
FIG. 2 is a view similar to that of FIG. 1, but illustrating the application of the improved laryngoscope embodying the present invention to a patient.

Referring to the drawings, there is shown in FIGS. 3, 3A, and 4 an improved laryngoscope blade 10 embodying the present invention. As best seen in FIG. 3A the laryngoscope blade 10 comprises an essentially straight blade or shaft portion 10A. The inner end portion 10B of the blade 10, adapted to be received in the patient's mouth, is curved out of the plane of the straight portion 10A. Referring to FIG. 2, the inner end 10B is curved so that in use, the curved inner end 10B is shaped so as to be received in the groove 11 defined between the base of the tongue 12 and the epiglottis 13. The tip end of the curved portion 10B is provided with a blunt tip or thickened bead 14 which extends transversely of the blade 10.

As seen in FIG. 3A the curved tip portion 10B is angled at approximately 30° relative to the straight portion 10A of the blade 10; the curved portion 10B extending along the inner 3 to 5 cms of the blade as indicated by dimension X. The tip end 14 is elevated out of the plane of the straight portion approximately 1.5 to 2 cms as indicated by dimension Y.

Depending along one edge of blade 10 is a lateral wall 15. Connected to the lower edge of the lateral wall and extending to one side thereof is a lateral shelf portion 16. The lateral shelf 16 extends substantially along the length of the straight blade portion 10A and it is of general uniform width, except that the shelf 16 gradually diminishes in width as it approaches the curved inner end 10B.

The outer end 10C of the blade 10 is provided with a detachable hinge recess 17 whereby it can be detachably hinged to a battery handle 18 of a well known construction. Mounted in the lateral wall of the blade 10 is a light bulb 19. It will be understood that the light bulb 19 is wired in circuit with the battery power source contained in the handle 18 of the laryngoscope.

Figure 1:
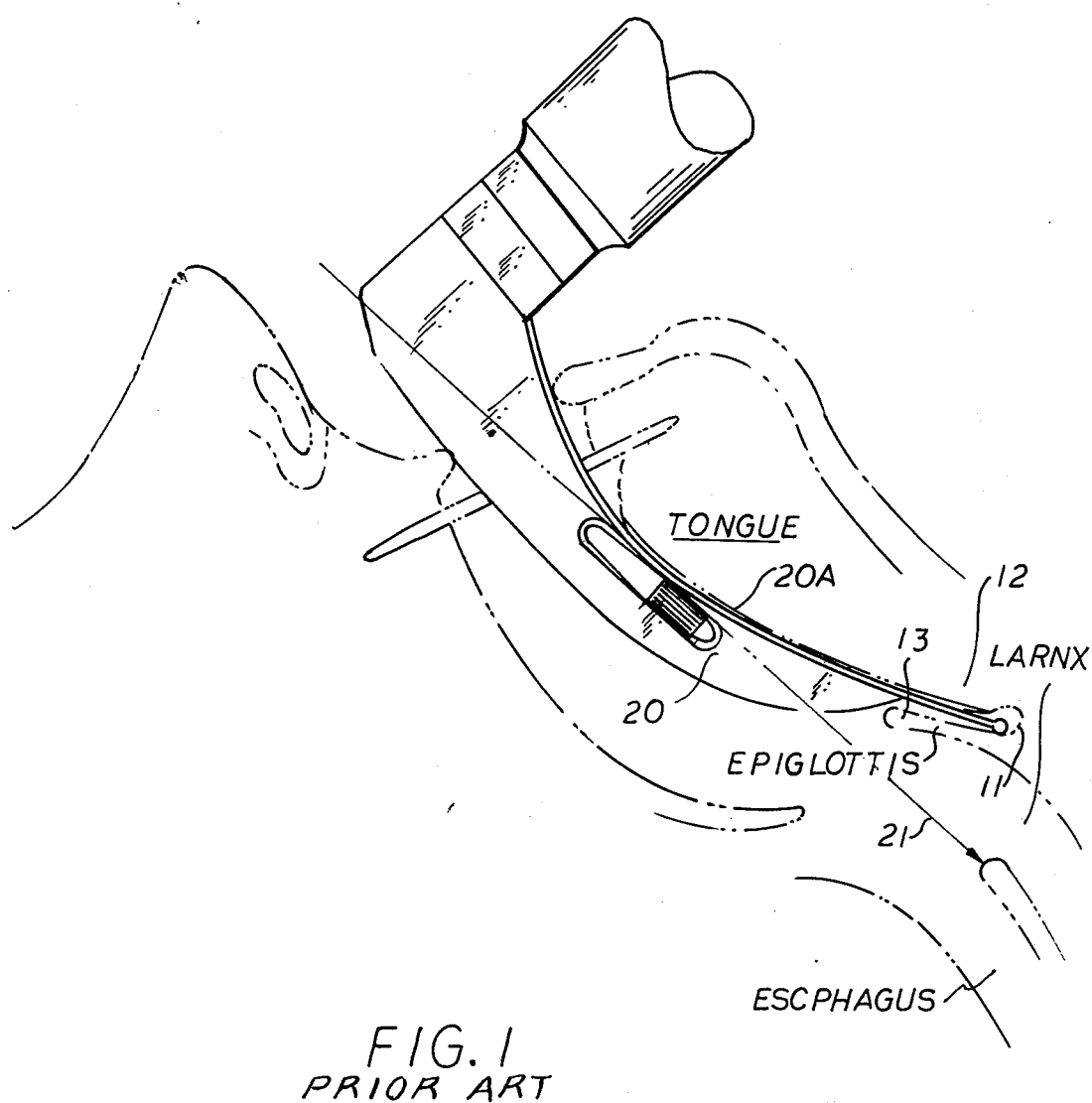
FIG. 1 is a diagrammatic showing illustrating the use of a prior art curved laryngoscope as applied to a patient.

In use, as best seen in FIG. 2, the inner end 10B of the blade 10 is inserted into a patient's mouth so that the inner end 10B of the blade is inserted in the groove or vallecula 11 between the base of the tongue 12 and the epiglottis 13. In doing so the base of the tongue tends to move anteriorly, i.e., upwardly in a patient who is lying down, causing the hyoid bone which is attached to the base of the tongue to move anteriorly with it. As the upper part of the epiglottis is fixed to the hyoid bone by the hyo-epiglottic ligament, the epiglottis moves up with the hyoid bone to expose the inlet of the larynx. For proper exposure of the larynx, the hyoid bone should be elevated anteriorly about 1.5 to 2 cms in an adult. With the inlet of the larynx thus exposed, the straight blade portion 10A defines a straight line of sight directly into the larynx as shown in FIG. 2 at 22. Since the described blade 10 does not touch the lower part of the epiglottis or the larynx, a laryngoscopy procedure can be done in a light plane of anethesia which is generally safer for the patient As a comparison, FIG. 1 illustrates how the curvature of the known prior art curved blades 20 obstruct vision to the larynx. While the curve blade 20 of prior art construction expose the larynx, the exposure was not such that a direct line of sight could be made to the larynx. Due to the curvature of the blade 20 throughout its length, the central curved portion 20A obstructed the vision by protruding into the lines of sight 21 to the larynx. Thus, as seen in FIG. 1, the central curved portion 20A caused the line of sight 21 to be lowered as compared to the line of sight 22 afforded by the blade 10 of this invention. By enhancing the exposure of the larynx, easier endotracheal intubatious can be had.

FIG. 5 illustrates a modified embodiment of the invention. In this form, the blade 30 is similar in all respects to that hereinbefore described except that the cross-sectional shape of the blade is modified. As shown in FIG. 5, the shaft portion 30A and connected lateral wall portion 30B defines an arcuate portion of a cylindrical shaft. The lateral shelf 30C, which is a continuation of the cylindrical shaft, is outwardly turned. In all other respects the structure and function of blade 30 is similar to that hereinbefore described.

FIG. 6 illustrates another slightly modified blade construction 35. In this form the cross-section of the blade includes a straight blade portion which is arcuate in cross-section as noted at 35A. The lateral wall 36 depends vertically from one edge of the arcuate blade shaft 35A and the lateral shelf 37 extends outwardly to one side of the lateral wall 36. In all other respects the structure and mode of use is similar to that hereinbefore described with respect to FIG. 1.

While the present invention has been described with respect to several embodiments thereof, it will be appreciated and understood that variations and modifications may be made without departing from the spirit and scope of the invention.

What is claimed is:

1. A laryngoscope blade comprising:
   a straight blade portion,
   said straight blade portion terminating in an inner end portion which angles out of the plane of said straight blade portion in a Y axis of the blade a distance ranging between 1.5 to 2 cms.,
   said inner end portion extending along the X axis of the blade a distance ranging between 3 to 5 cms., whereby said inner end portion can be inserted into a vallecular groove so as to cause anterior movement of the hyoid bone in the operative position of said laryngoscope blade to effect anterior displacement of the epiglottis to expose the inlet of the larynx,
   said straight blade portion compressing the tongue whereby the co-action between said straight portion and angled inner end acting on said tongue and hyoid bone and connected epiglottis respectfully defines a straight wide angle line of sight directly into the larynx,
   a lateral wall connected along one edge of said straight blade portion,
   a lateral shelf connected to the other end of said lateral wall,
   said lateral shelf extending in a direction opposite to said straight blade portion whereby said straight blade portion and shelf portion are disposed in substantially spaced apart parallel planes.

2. The invention as defined in claim 1 wherein:
   said straight blade portion is accurate in cross-section to define a semi-cylindrical like shaft,
   and said shaft having a lateral outwardly turned edge to define lateral shelf.

3. A laryngoscope blade adapted to be pivotally connected to a battery handle comprising:
   a blade portion,
   a lateral wall connected along one edge of said blade portion,
   said lateral wall being disposed substantially normal to said blade portion, and said blade portion extending laterally to one side of said lateral wall,
   a lateral shelf connected to the other end of said lateral wall,
   said lateral shelf having disposed substantially normal to said lateral wall, and said lateral shelf extending to the other side of said lateral wall,
   said blade portion being essentially straight and flat along a major length thereof, said straight blade portion and lateral shelf portion being disposed in substantially spaced apart parallel planes,
   said blade portion having inner end portion extending out of the plane of said straight blade portion over the inner 3 to 5 cms of said laryngoscope blade to form a continuation of said essentially straight portion,
   said inner end portion terminating in a thickened tip disposed approximately 1.5 to 2 cm out of the plane of said straight blade portion,
   said inner end portion being proportioned to be inserted in the vallecula defined between the base of tongue and the epiglottis whereby the hyoid bone and connected epiglottis is caused to be moved anteriorly to expose the inlet of the larynx so that said straight portion of the blade is in alignment with the larynx to define a wide angle line of sight into said exposed larynx,
   and a light bulb mounted on the lateral wall.

* * * * *